United States Patent [19]

Davis

[11] Patent Number: 4,767,751
[45] Date of Patent: Aug. 30, 1988

[54] TOPICAL DRUG RELEASE SYSTEM

[75] Inventor: Adrian F. Davis, Dorking, England

[73] Assignee: Beecham Group p.l.c., England

[21] Appl. No.: 693,770

[22] Filed: Jan. 23, 1985

[30] Foreign Application Priority Data

Jan. 25, 1984 [GB] United Kingdom ............... 8401965

[51] Int. Cl.⁴ .............................................. A61K 31/56
[52] U.S. Cl. .................................... 514/179; 514/561; 514/570; 514/629; 514/721; 514/937; 514/944
[58] Field of Search ......................... 514/179, 944, 937

[56] References Cited

U.S. PATENT DOCUMENTS

| | | | |
|---|---|---|---|
| 4,140,656 | 2/1979 | Mast | 252/545 |
| 4,244,942 | 1/1981 | Kamishita et al. | 424/81 |
| 4,602,040 | 7/1986 | Belsoce | 514/567 |

FOREIGN PATENT DOCUMENTS 1582207  7/1981  United Kingdom .

OTHER PUBLICATIONS

Coldman et al., J. Pharm. Sci., vol. 58, No. 9(1969), pp. 1098-1102.
Umer, Chem. Abst., 97, 188191t (1982).

*Primary Examiner*—Leonard Schenkman
*Attorney, Agent, or Firm*—Jacobs & Jacobs

[57] ABSTRACT

A pharmaceutical composition for topical administration consisting of two liquid phases designed to be admixed in situ or prior to use. The first phase contains a dissolved drug, and is preferably saturated in the drug, while the second phase is a chemically or physically different liquid from that in the first phase and contains no drug, but is miscible with the first phase. The two liquids are selected so that, on admixture of suitable volumes of the phases, the resultant drug concentration exceeds the saturated drug solubility in the resultant mixture. This produces a liquid mixture supersaturated in drug, which has been found to increase the rate of drug penetration into the skin. The two liquid phases may be gels, and the drug may be hydrocortisone.

17 Claims, No Drawings

TOPICAL DRUG RELEASE SYSTEM

The present invention relates to a pharmaceutical composition, and in particular to a composition for topical application to the human or animal body.

Hitherto, high levels of a pharmaceutically active material (hereinafter referred to as 'the drug') have often been incorporated into a liquid carrier by forming a saturated solution of the drug in the carrier, thereby providing an effective topical treatment composition.

It has also been proposed (J. Pharm. Sci. Vol. 58, No. 9 (1969) pp 1098–1102; Coldman et al) to create a supersaturated solution of the drug from a subsaturated solution of the drug in a mixture of a volatile and a non-volatile solvent. On topical application of the solution, the volatile solvent rapidly evaporates, thereby increasing the drug concentration to a supersaturated level. This has been found to increase the rate of drug penetration into the skin.

It has now been found that improved drug penetration can be obtained by creating a supersaturated drug solution in situ without the need for volatile solvent evaporation. This enables a wide range of drugs and carrier systems to be employed for many different types of topical treatments.

According to the present invention there is provided a pharmaceutical composition for topical application, comprising a first liquid phase containing a drug dissolved therein, and a second liquid phase, physically and/or chemically different from the first phase but miscible therewith, optionally containing the same drug dissolved therein, the concentration of drug in each phase and the composition of the phases being such that, on admixture of the phases, the resultant total drug concentration is greater than the saturated drug solubility in the initially formed resultant mixture, thereby producing a mixture supersaturated with the drug.

The term 'liquid' is used herein to include viscous materials such as creams, ointments or gels.

The relative proportions by volume of the first liquid phase to the second liquid phase is suitably from 1:1 to 1:9 more suitably from 1:1 to 1:3.

The second phase need not contain any drug, provided the resultant mixture is supersaturated in drug.

Each phase may contain two or more drugs, in amounts such that the resultant mixture is supersaturated in one or more drugs.

Preferably, the first phase comprises a suitable solubiliser optionally in admixture with a pharmaceutically acceptable carrier and the second phase comprises a pharmaceutically acceptable carrier optionally in admixture with a suitable solubiliser.

Examples of solubilisers are propylene glycol, 1,3-propylene diol, polyethylene glycol, ethanol, propanol, glycerine, dimethyl sulphoxide, dimethyl acetamide, dimethyl formamide, higher alcohols, higher carboxylic acids, fatty esters, mineral and vegetable oils and mixtures of any thereof. Examples of suitable higher alcohols or carboxylic acids include those having from 12–18 carbon atoms such as lauryl or steryl derivatives. Examples of suitable fatty esters include isopropylmyristate and glyceryl mono-esters. Examples of suitable mineral and vegetable oils include liquid paraffin, castor oil, soyabean oil, olive oil etc.

In the case of ionisable drugs, aqueous acid or alkali buffers are also useful as solubilisers. Preferably the first phase comprises from 0 to 50% of carrier, and from 50 to 100% of solubiliser, and the second phase comprises from 0 to 50% of solubiliser, and from 50 to 100% of carrier.

The carrier is suitably a liquid which is miscible with the solubiliser but which has a different lipophilicity. A preferred carrier when the solubiliser is not a higher alcohol or carboxylic acid, a fatty ester or a mineral or vegetable oil comprises water. When the solubiliser is a higher alcohol, a higher carboxylic acid, a fatty ester or a mineral or vegetable oil the carrier is preferably a lower alcohol or polyol such as propylene glycol, 1,3-propylene diol, polyethylene glycol ethanol or propanol.

Preferably, the first phase comprises a mixture of carrier and solubiliser, and the second phase comprises the same carrier, optionally admixed with the same solubiliser in a different weight ratio from the carrier:-solubiliser weight ratio of the first phase.

It has been found advantageous to form the first phase and second phase so that the drug is initially saturated in the first phase but is absent from the second phase. The degree of supersaturation, and hence rate of drug release, of the final mixture can then easily be predicted from the saturated drug solubility curve for the particular solubiliser/carrier system.

The degree of improvement in drug penetration rate in situ will depend largely on the ratio of supersaturated drug concentration to saturated drug concentration. A ratio of greater than 1:1 is considered useful and ratios of from 2:1, for relatively slow penetration, to 10:1, for rapid penetration, are preferred. By means of the present invention, extremely high degrees of supersaturation can be obtained, and ratios of 50:1 or greater are achievable. Due to the inefficency of percutaneous absorption, such highly supersaturated systems would be of great benefit.

Each phase may be thickened with a suitable thickening or gelling agent of either natural or synthetic origin. Examples of thickening and gelling agents are natural gums, tragacanth, carrageen, pectin, agar, alginic acid, cellulose ethers and esters, xanthan gum, guar and locust bean gum, Bentonite (a colloidal hydrate aluminium silicate), Veegum (colloidal magnesium aluminium silicate), Laponite (a synthetic hectorite), polyvinyl alcohol, Aerosil (a trademark, colloidal silica) and Carbopol (a trademark).

The composition of the invention may be packaged into a twin compartment pack ready for topical application by a patient. The patient would normally apply the two phases simultaneously to the treatment area, and then mix the phases together in situ to create the supersaturated drug system.

The two phases may also be mixed in the pack by breaking a membrane separating the phases, and can then be dispensed from the pack as a supersaturated drug system.

Suitable packs for these purposes are commercially available and respective examples are (i) the dual tube 'Tube-in a Tube' (manufactured by Metal Box) and (ii) the 'Panmix' twin compartment pack (manufactured by Panpack Limited). ('Panmix' is a trade mark).

Alternatively, the two phases may be packed into a single compartment, according to the method described in UK Patent Specification No. 962,757. In this case, the two phases must have sufficiently high viscosity to emerge from the compartment as a single extruded mass, and the phases should of course be stable at their interface when stored inside the compartment.

The pharmaceutical composition of the invention is suitable for any medical treatment of the body surface, including the skin, scalp, nails and oral mucosa. It is also envisaged that the composition will be of value in treating systemic diseases by the so called transdermal route. At present, only well absorbed or very low dose drugs have been found useful in transdermal systems. The composition of the present invention provides a means by which many drugs, which are not particularly well absorbed or need to be delivered in high doses, can be administered effectively in a transdermal system. The phases can be mixed within a transdermal device such as the Transiderm-Nitro (a trade mark) immediately before application to the skin.

Accordingly, in a further aspect the invention provides a transdermal device containing a pharmaceutical composition according to the invention.

Suitable drugs for use in the composition of the invention are many and varied, and include the following types, with specific examples of each in brackets:

Steroid (hydrocortisone); Anti-bacterial (tetracycline); Anti-septic (chlorohexidine); Anti-fungal (econazole); Anti-psoriasis (dithranol); Anti-acne (retinoic acid); Anti-dandruff (zinc omadine); treatment of headlice (acaricide); Anti-histamine (mepyramine); Local anaesthetic (benzocaine or lignocaine); Analgesic, anti-inflammatory (ibuprofen).

The invention will now be illustrated by means of the following Examples.

For use in a transdermal device, the following drugs, would be suitable examples: beta-adrenoceptor blockers (propanolol), broncho-spasm relaxants (theophylline), anti-angina (glyceryl trinitrate), anti-travel sickness (scopolamine), anti-histamine (chlorpheniramine), decongestants (phenylpropanolamine), anti-tussive (pholcodine), analgesic (codeine, flurbiprofen) and anti-coagulant (warfarin).

EXAMPLE 1

(a) Preparation of Hydrocortisone Carbopol Gel System

The saturated solubility of hydrocortisone in a water/propylene glycol cosolvent system was determined over the range 0% to 90% propylene glycol. The results were used as a basis to formulate Carbopol gel systems.

Referring to Table 1 below, a hydrocortisone-saturated Carbopol gel system (Gel B) and a gel system containing no hydrocortisone (Gel A) were mixed together in weight proportions of 34.5% Gel B: 65.5% Gel A to produce Gel C, a 0.5% concentration hydrocortisone gel, approximately four-fold supersaturated in hydrocortisone.

A second hydrocortisone-saturated Carbopol gel system (Gel E) was prepared to give a gel with the same concentration, 0.5%, as in the supersaturated gel produced by mixing Gels A and B as above.

TABLE 1

| Ingredient | Gel A % w/w | Gel B % w/w | Gel C % w/w (65.5: Gel A) (34.5: Gel B) | Gel E % w/w |
|---|---|---|---|---|
| Hydrocortisone | — | 1.45 | 0.50 | 0.50 |
| Propylene glycol | — | 86.10 | 29.50 | 55.0 |
| Distilled water | 97.0 | 9.45 | 67.00 | 41.50 |
| *Carbopol 940 | 1.0 | 1.0 | 1.0 | 1.0 |
| Di-isopropano-lamine | 2.0 | 2.0 | 2.0 | 2.0 |
|  | 100 | 100 | 100 | 100 |

*Supplied by Goodrich Chemicals

(b) Preparation Details (i) Gels B and E

The hydrocortisone was dissolved in the propylene glycol. The Carbopol 940 was mixed into the water to give a lump-free, cloudy dispersion and added to the hydrocortisone in propylene glycol with mixing. Di-isopropanolamine was added (for neutralisation) to give a clear viscous gel.

(ii) Gel A

The Carbopol was dispersed in water and neutralised with di-isopropanolamine.

(c) Results of In-vitro Release of Hydrocortisone from Carbopol Gel Systems

The procedure used for examining hydrocortisone release from Carbopol gels was reported by Poulsen BJ et al. (J. Pharm Sci 1968; 57 (6): 928–933). Release into isopropyl myristate is used as a model of release into the skin.

Hydrocortisone was assayed following its release into isopropyl myristate using a normal phase HPLC system.

The following two gel systems were examined.

Gel C: 0.5% concentration hydrocortisone in a base comprising 29.50 m propylene glycol to 67.00 water, (approximately four-fold supersaturated).

Gel E: 0.5% concentration hydrocortisone in a base comprising 55.00 propylene to 41.50 water, (approximately saturated).

The results are shown in Table 2.

TABLE 2

| Total amount of hydrocortisone released, mg | Release of Hydrocortisone into Isopropyl Myristate | | | | | | | | | |
|---|---|---|---|---|---|---|---|---|---|---|
| | Time (minutes) | | | | | | | | | |
| | 15 | 30 | 45 | 60 | 90 | 120 | 180 | 240 | 300 | 360 |
| Gel C, 0.5%, supersaturated | 2.55 | 3.73 | 5.24 | 6.90 | 9.38 | 11.80 | 15.80 | 17.60 | 19.87 | 22.36 |
| Gel E, 0.5%, saturated | 0.83 | 1.10 | 1.34 | 2.01 | 2.20 | 2.66 | 3.95 | 4.96 | 5.41 | 6.52 |

Conclusions

In-vitro release from the supersaturated gel, Gel C, is from three to four-fold better than from the saturated gel Gel E.

EXAMPLE 2

(a) Preparation of Ibuprofen Carbopol Gel System

Referring to Table 3 below, by mixing together an approximately saturated ibuprofen gel system (Gel B) and a gel system containing no ibuprofen (Gel A) in equal proportions, a 1% ibuprofen gel of approximately twelve-fold supersaturation (Gel C) was produced. The various gels were made in a similar manner to those of example 1.

TABLE 3

| Ingredient | Gel A % w/w | Gel B % w/w | Gel C (50: Gel A) (50: Gel B) % w/w |
|---|---|---|---|
| Ibuprofen | — | 2 | 1.0 |
| Propylene glycol | — | 77.20 | 38.60 |
| Distilled water | 98.5 | 19.30 | 58.90 |
| Carbopol 940 | 1.0 | 1.0 | 1.0 |
| Di-isopropanolamine | 0.5 | 0.5 | 0.5 |
|  | 100 | 100 | 100 |

EXAMPLE 3

(a) Preparation of Triclosan Carbopol Gel System

Referring to Table 4 below, by mixing together a subsaturated triclosan (Gel A) in equal proportions a 0.5% triclosan gel of approximately fifteen-fold supersaturation (Gel C) can be produced.

TABLE 4

| Ingredient | Gel A % w/w | Gel B % w/w | Gel C (50: Gel A) (50: Gel B) % w/w |
|---|---|---|---|
| Triclosan | — | 1.0 | 0.5 |
| Ethanol | — | 57.60 | 28.8 |
| Distilled water | 97 | 38.40 | 67.7 |
| Carbopol 940 | 1 | 1 | 1 |
| Di-isopropanolamine | 2 | 2 | 2 |
|  | 100 | 100 | 100 |

(b) Preparation Details

As described in example 1, but using ethanol as cosolvent.

In the examples described above, drugs with positive log partition coefficient are dissolved in cosolvent rich systems and water systems are added to cause formation of a supersaturated system. However, a "reverse" effect can be obtained by dissolving drugs with negative partition coefficients in water and then adding cosolvent rich systems to cause formation of a supersaturated systems. This is illustrated by the following Example 4.

EXAMPLE 4

(a) Preparation of Glycine Carbopol Gel System

Referring to Table 5 below, by mixing together an approximately saturated glycine gel system (Gel A) and a gel system containing no glycine in a ratio of 1:3, a 4% glycine gel having approximately four-fold supersaturation (Gel C) can be produced.

TABLE 5

| Ingredient | Gel A % w/w | Gel B % w/w | Gel C (25: Gel A) (75: Gel B) % w/w |
|---|---|---|---|
| Glycine | 16 | — | 4 |
| Ethanol | — | 97 | 73.50 |
| Distilled water | 83 | — | 20.50 |
| Carbopol 940 | 1 | 1 | 1 |
| Di-isopropanolamine | 0 | 2 | 1 |
|  | 100 | 100 | 100 |

(b) Preparation Details

As described in example 1, but using ethanol as cosolvent.

What is claimed is:

1. A pharmaceutical composition for topical application, comprising a first liquid phase and a second liquid phase different from the first phase but miscible with the first phase upon admixture therewith, at least one of said phases comprising a drug dissolved therein, the concentration of said drug in each phase in which said drug is present and the composition of the phases being such that, on admixture of the phases, the total drug concentration in the initially formed resultant mixture is greater than the saturated drug solubility in said initially formed resultant mixture, whereby said resultant mixture is supersaturated with the drug.

2. A composition according to claim 1, in which the first phase comprises a solubiliser, and the second phase comprises a pharmaceutically acceptable carrier.

3. A composition according to claim 2, in which the first phase comprises a mixture of a pharmaceutically acceptable carrier and said solubiliser, and the second phase comprises the same carrier.

4. A composition according to claim 1, in which the first phase comprises up to 50% of carrier, and from 50 to 100% of solubiliser, and the second phase comprises up to 50% solubiliser, and from 50 to 100% of carrier.

5. A composition according to claim 2, in which the solubiliser is propylene glycol, 1,3-propylene diol, polyethylene glycol, ethanol, propanol, glycerine, dimethyl sulphoxide, dimethyl acetamide, dimethylformamide, higher alcohol, higher carboxylic acid, fatty ester, mineral oil, vegetable oil, aqueous acid or an alkali buffer.

6. A composition according to claim 1 in which the drug is initially saturated in the first phase and is absent from the second phase.

7. A composition according to claim 1 in which the ratio of supersaturated drug concentration in said resultant mixture to saturated drug concentration in said resultant mixture is from 2:1 to 50:1.

8. A composition according to claim 1, in which the drug is hydrocortisone, ibuprofen, lignocaine, triclosan or glycine.

9. A twin compartment pack containing a composition according to claim 1, the first liquid phase being in one compartment and the second liquid phase being in the other compartment.

10. A transdermal device containing a composition according to claim 1.

11. A composition according to claim 3, in which said second phase comprises a mixture of said carrier and a solubiliser.

12. A composition according to claim 11, in which said second phase comprises a solubiliser which is the same as the solubiliser in the first phase but in a different weight ratio of carrier:solubiliser than in the first phase.

13. A composition according to claim 1, wherein said second phase also contains said drug dissolved therein.

14. A method for topical application of the pharmaceutical composition of claim 1, which comprises mixing said liquid phases to form a mixture supersaturated with said drug, and applying said mixture to the skin.

15. A method for topical application of the pharmaceutical composition of claim 1, which comprises applying said liquid phases to the skin and admixing said liquid phases to form on the skin a mixture supersaturated with said drug.

16. A method for topical application of the pharmaceutical composition contained in the twin-compartment pack of claim 9, which comprises mixing said liquid phases within said pack to form therein a mixture supersaturated with said drug and dispensing said mixture from said pack to the skin.

17. A method for the topical administration of the pharmaceutical composition contained in the transdermal device of claim 10, which comprises mixing said liquid phases within said device to form therein a mixture supersaturated with said drug, and thereafter operatively applying said device to the skin.

* * * * *